US00PP34448P2

(12) United States Plant Patent
Snijder

(10) Patent No.: US PP34,448 P2
(45) Date of Patent: Jul. 26, 2022

(54) ***PELARGONIUM* PLANT NAMED 'PECZ0026'**

(50) Latin Name: ***Pelargonium* x *hortorum***
Varietal Denomination: 'PECZ0026'

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/354,294

(22) Filed: Jun. 22, 2021

(51) Int. Cl.
*A01H 5/02* (2018.01)
*A01H 6/42* (2018.01)

(52) U.S. Cl.
USPC ..... Plt./326
CPC ..... *A01H 6/425* (2018.05)

(58) Field of Classification Search
USPC ..... Plt./326
CPC ..... A01H 6/425; A01H 5/02
See application file for complete search history.

*Primary Examiner* — Anne Marie Grunberg
(74) *Attorney, Agent, or Firm* — Dale Skalla

(57) ABSTRACT

A new *Pelargonium* plant named 'PECZ0026' particularly distinguished by white colored inflorescences with single florets with fringed upper petals, held above medium green foliage, on an upright-mounding branched vigorous plant with fan-shaped leaves and very free flowering, sun and heat tolerant habit.

1 Drawing Sheet

Latin name of the genus and species of the plant claimed: *Pelargonium* x *hortorum.*

Varietal denomination: 'PECZ0026'.

BACKGROUND OF THE NEW PLANT

The present invention comprises a new *Pelargonium,* botanically known as *Pelargonium* x *hortorum*, and hereinafter referred to by the variety name 'PECZ0026'.

'PECZ0026' is a product of a planned breeding program. The new cultivar 'PECZ0026' has white colored inflorescences with single florets with fringed upper petals, held above medium green foliage, on an upright-mounding branched vigorous plant with fan-shaped leaves and very free flowering, sun and heat tolerant habit.

'PECZ0026' originates from a self-pollination in a controlled breeding program made in July 2013, in a greenhouse in Enkhuizen, The Netherlands. The parent was an unpatented plant of *P.* x *hortorum* parentage identified as 'PEL-AZ3241-01V' with larger and rounder florets, as well as more petal pigmentation when compared to 'PECZ0026'.

'PECZ0026' was selected as one flowering plant within the progeny of the stated cross in May 2014 in a greenhouse in Enkhuizen, The Netherlands.

The first act of asexual reproduction of 'PECZ0026' was accomplished when vegetative cuttings were propagated from the initial selection in June 2014 in a greenhouse in Enkhuizen, The Netherlands.

BRIEF SUMMARY OF INVENTION

Horticultural examination of plants grown from cuttings of the plant initiated in May 2015 in Enkhuizen, The Netherlands and continuing thereafter, has demonstrated that the combination of characteristics as herein disclosed for 'PECZ0026' are firmly fixed and are retained through successive generations of asexual reproduction.

'PECZ0026' has not been observed under all possible environmental conditions. The phenotype may vary significantly with variations in environment such as temperature, light intensity, and day length.

A Plant Breeder's Right for this cultivar has not yet been applied for. 'PECZ0026' has not been made publicly available prior to the effective filing date of this application, notwithstanding any disclosure that may have been made less than one year prior to the effective filing date of this application by the inventor or another who obtained 'PECZ0026' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PECZ0026' with colors being as true as possible with an illustration of this type.

Figure 1:
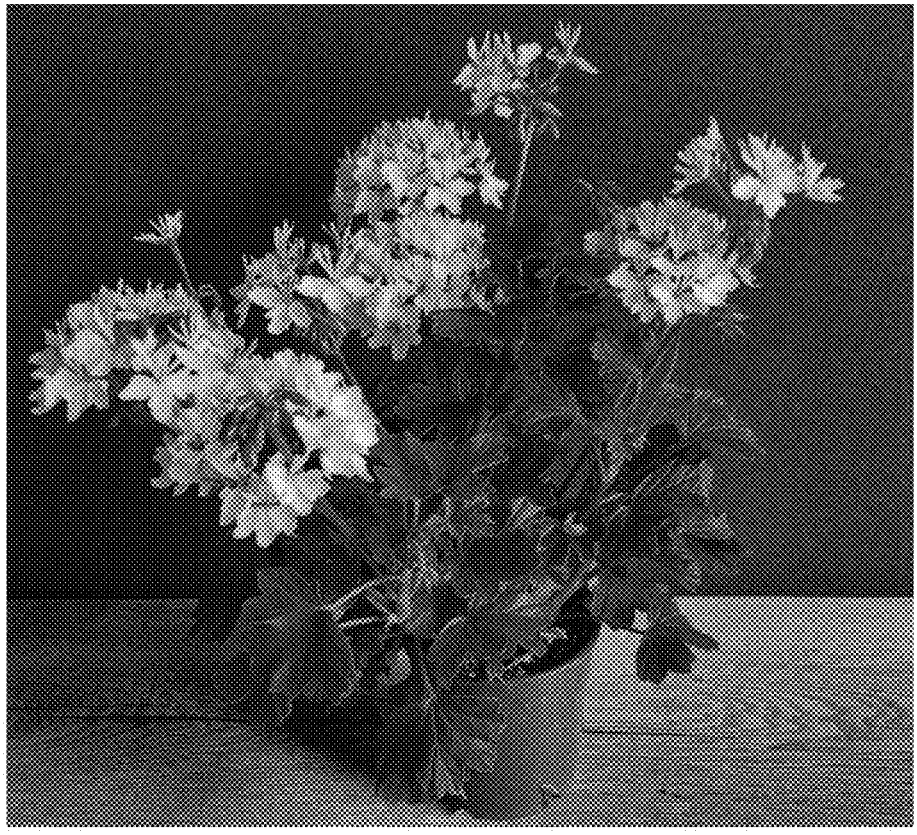
Figure 2:
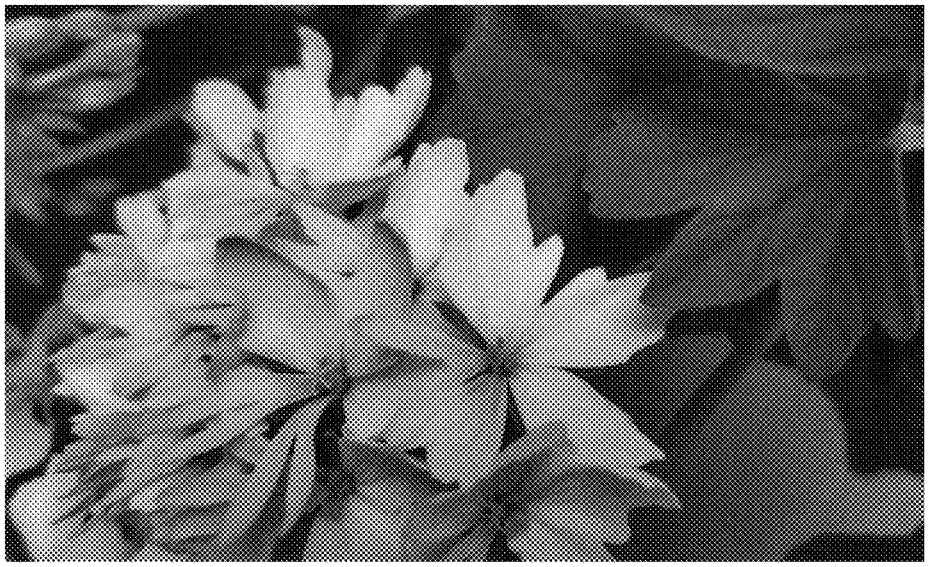

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in early June 2021 under natural light. These plants were approximately 16 weeks old and were grown in a 12 cm pot, in a greenhouse trial. The photographs were taken in June 2021.

Color references are made to The Royal Horticultural Society Colour Chart (RHS) 2001.

TABLE 1

DIFFERENCES BETWEEN THE NEW VARIETY 'PECZ0026' AND A MOST SIMILAR VARIETY

| | 'PECZ0026' | 'Grawit' (U.S. Plant Pat. No. 18,773) |
|---|---|---|
| Petal color: | Stable white color throughout season no fading | Slightly infused with pink |

Plant:
- *Form, growth and habit.*—Upright-mounding.
- *Plant height.*—18-21 cm.
- *Plant height (inflorescence included).*—25-28 cm.
- *Plant width.*—29-33 cm.

Roots:
- *Number of days to initiate roots.*—15-18 days at about 22 degrees C.
- *Number of days to produce a rooted cutting.*—21-23 days at 22 degrees C.
- *Type.*—Fine, fibrous, free branching.
- *Color.*—RHS N155B but whiter.

Foliage:
- *Variegation.*—Absent.
- *Immature leaf, color upper surface.*—Closest to RHS 137B.
- *Immature leaf, lower surface.*—Closest to RHS 138B.
- *Mature leaf, color upper surface.*—Closest to RHS 137A.
- *Mature leaf, color lower surface.*—Closest to RHS 138B.
- *Length.*—4.5-5 cm.
- *Width.*—7.5-8.5 cm.
- *Shape.*—Palmatifid.
- *Base shape.*—Mostly truncate, slightly cordate.
- *Sinus of mature leaf.*—Mostly shallow, incised one tenth of the leaf length, up to maximum medium shallow, incised one-third of the leaf length.
- *Leaf base openness.*—Wide open.
- *Apex shape.*—Acute.
- *Margin.*—Dentate.
- *Texture upper side.*—Hirsute.
- *Texture lower side.*—Hirsute.
- *Leaf zonation color.*—None.
- *Color of veins, upper surface.*—RHS 137A, largely indistinct.
- *Color of veins, lower surface.*—RHS 144B, becoming indistinct.
- *Pattern of veining.*—Palmate.
- *Petiole color.*—RHS 143C.
- *Petiole length.*—6-7 cm.
- *Diameter of petiole.*—0.2 cm.
- *Texture.*—Pilose, hirsute, glandular hairs.

Stem:
- *Quantity of branches.*—6-10.
- *Color of stem.*—Close to RHS 143B.
- *Anthocyanin coloration of stem.*—Absent anthocyanin coloration is visible under high solar radiation.
- *Length of stem.*—9-17 cm.
- *Diameter.*—0.5 cm.
- *Length of internodes.*—1-4 cm.
- *Texture.*—Sparsely hirsute, pilose, glandular hairs.

Peduncle:
- *Color of peduncle.*—RHS 144A.
- *Length of peduncle.*—12-18 cm.
- *Peduncle diameter.*—0.3-0.4 cm.
- *Texture.*—Hirsute, glandular hairs.
- *Anthocyanin coloration of peduncle.*—Absent.

Pedicel:
- *Color of pedicel.*—RHS 143B.
- *Length of pedicel.*—3-3.5 cm.
- *Diameter of pedicel.*—0.15-0.2 cm.
- *Texture.*—Sparsely pilose, glandular hiars.
- *Pedicel swelling.*—Swelling was not observed.

Bud (just before opening):
- *Color.*—RHS 157D.
- *Length.*—0.8-1.2 cm.
- *Width.*—0.4-0.5 cm.
- *Shape.*—Elliptical.

Inflorescence:
- *Type.*—Umbel; semi-spherical or nearly semi-spherical.
- *Lastingness of individual flowers.*—7-9 days at 18° C. temperature.
- *Number of inflorescences per plant.*—6-12, with 5-12 immature umbels in various stages.
- *Average total number of buds.*—35.
- *Fragrance.*—None.
- *Umbel diameter.*—8-10 cm.
- *Umbel depth.*—6-9 cm.

Corolla:
- *Form.*—Single.
- *Number of petals.*—5.
- *Diameter of flower.*—3-3.5 cm.
- *Depth of flower.*—1.5 cm.
- *Side view shape.*—Concave.
- *Color upper petals, upper surface.*—Whiter than RHS N155B.
- *Color upper petals, lower surface.*—Whiter than RHS N155A.
- *Length of upper petals.*—1.5-2.2 cm.
- *Width of upper petals.*—0.5-0.6 cm.
- *Color lower petals, upper surface.*—Whiter than RHS N155B.
- *Color lower petals, lower surface.*—Whiter than RHS N155A.
- *Markings on upper petals.*—None.
- *Markings on lower petals.*—None.
- *Length of lower petals.*—2.4-2.6 cm.
- *Width of lower petals.*—1.7-1.8 cm.
- *Petal shape.*—Obovate to spathulate.
- *Apex shape.*—Rounded.
- *Margin.*—Dentate.
- *Base.*—Attenuate.
- *Petal texture.*—Papillose on both surfaces.

Calyx:
- *Number of sepals.*—5.
- *Color of sepals.*—RHS 144B, veins RHS 144A.
- *Length of sepals.*—0.9-1.1 cm.
- *Width of sepals.*—0.1-0.3 cm.
- *Sepal shape.*—Lanceolate to linear.
- *Apex shape.*—Acute.
- *Margins.*—Mostly fused.
- *Texture, upper surface.*—Glabrous.
- *Lower surface.*—Glandular hairs, hirsute.
- *Sepal flexing.*—Mostly unflexed sepals. The narrowest sepals flex moderately.

Reproductive organs:

Gynoecium:
- *Pistil.*—RHS 157C.
- *Length.*—0.6-0.7 cm.

*Style color.*—RHS 157C.
*Style length.*—0.2-0.3 cm.
*Stigma color.*—RHS 157C.
*Ovary color.*—RHS 144C.
*Ovary length.*—0.3 cm.
*Ovary diameter.*—0.2 cm.

Androecium:

*Number of stamens.*—5 with 2 staminoids.
*Color of filaments.*—RHS 157C.
*Length filaments.*—0.6 cm.
*Anther color.*—RHS 171C.
*Length of anthers.*—0.15 cm.
*Color of pollen.*—RHS 28A.
*Pollen amount.*—Abundant.
*Fertility/seed set.*—Fertile.
*Botanical description of the fruit and seed.*—Not observed on this hybrid.
*Disease/pest resistance.*—Has not been determined to date.

What is claimed is:

1. A new and distinct variety of *Pelargonium* plant named 'PECZ0026' substantially as illustrated and described herein.

* * * * *